United States Patent [19]

Shibamoto

[11] Patent Number: 5,672,810
[45] Date of Patent: Sep. 30, 1997

[54] GAS CHROMATOGRAPH APPARATUS FOR A LIQUID SAMPLE CONTAINING A SOLVENT

[75] Inventor: Shigeaki Shibamoto, Kyoto, Japan

[73] Assignee: Shimadzu Corporation, Kyoto, Japan

[21] Appl. No.: 649,768

[22] Filed: May 15, 1996

[30] Foreign Application Priority Data

Jul. 18, 1995 [JP] Japan ................... 7-205259

[51] Int. Cl.⁶ .................................. G01N 30/04
[52] U.S. Cl. .............. 73/23.25; 73/23.41; 73/23.42
[58] Field of Search ..................... 73/23.22, 23.25, 73/23.41, 23.42, 23.35

[56] References Cited

U.S. PATENT DOCUMENTS

| | | | |
|---|---|---|---|
| 3,057,183 | 10/1962 | De Ford | 73/23.22 X |
| 3,327,520 | 6/1967 | Stapp, Jr. | 73/23.25 X |
| 4,805,441 | 2/1989 | Sides et al. | 73/23.25 |
| 5,339,673 | 8/1994 | Nakagawa et al. | 73/23.42 X |
| 5,347,844 | 9/1994 | Grob et al. | 73/23.41 |
| 5,467,635 | 11/1995 | Nakagawa et al. | 73/23.42 X |
| 5,524,084 | 6/1996 | Wang et al. | 73/23.25 X |
| 5,545,252 | 8/1996 | Hinshaw et al. | 73/23.25 X |

FOREIGN PATENT DOCUMENTS

| | | | |
|---|---|---|---|
| 115972 | 5/1991 | Japan | 73/23.42 |
| 262964 | 11/1991 | Japan | 73/23.35 |
| 105062 | 4/1992 | Japan | 73/23.42 |
| 274759 | 9/1992 | Japan | 73/23.41 |

*Primary Examiner*—Hezron E. Williams
*Assistant Examiner*—Daniel S. Larkin
*Attorney, Agent, or Firm*—Majestic, Parsons, Siebert & Hsue

[57] ABSTRACT

A gas chromatograph for analyzing a selected target component in a liquid sample, which also contains a solvent, has a sample injection port, a temperature control unit, a split ratio control unit and a vaporization control unit. The sample injection port contains a pre-column filled with a packing material capable of holding a liquid sample injected into the pre-column. The sample injection port has a carrier gas inlet, a split vent, and an opening connected to a column. The temperature control unit is for controlling temperature of the sample injection port, and the split ratio control unit is for controlling the split ratio, defined as the ratio between gas flow rate to the column and the rate of the gas being discharged through the split vent. The vaporization control unit serves to control both the temperature control unit and the split control unit in coordination with each other according to the boiling points of the target component and the solvent in the liquid sample.

6 Claims, 2 Drawing Sheets

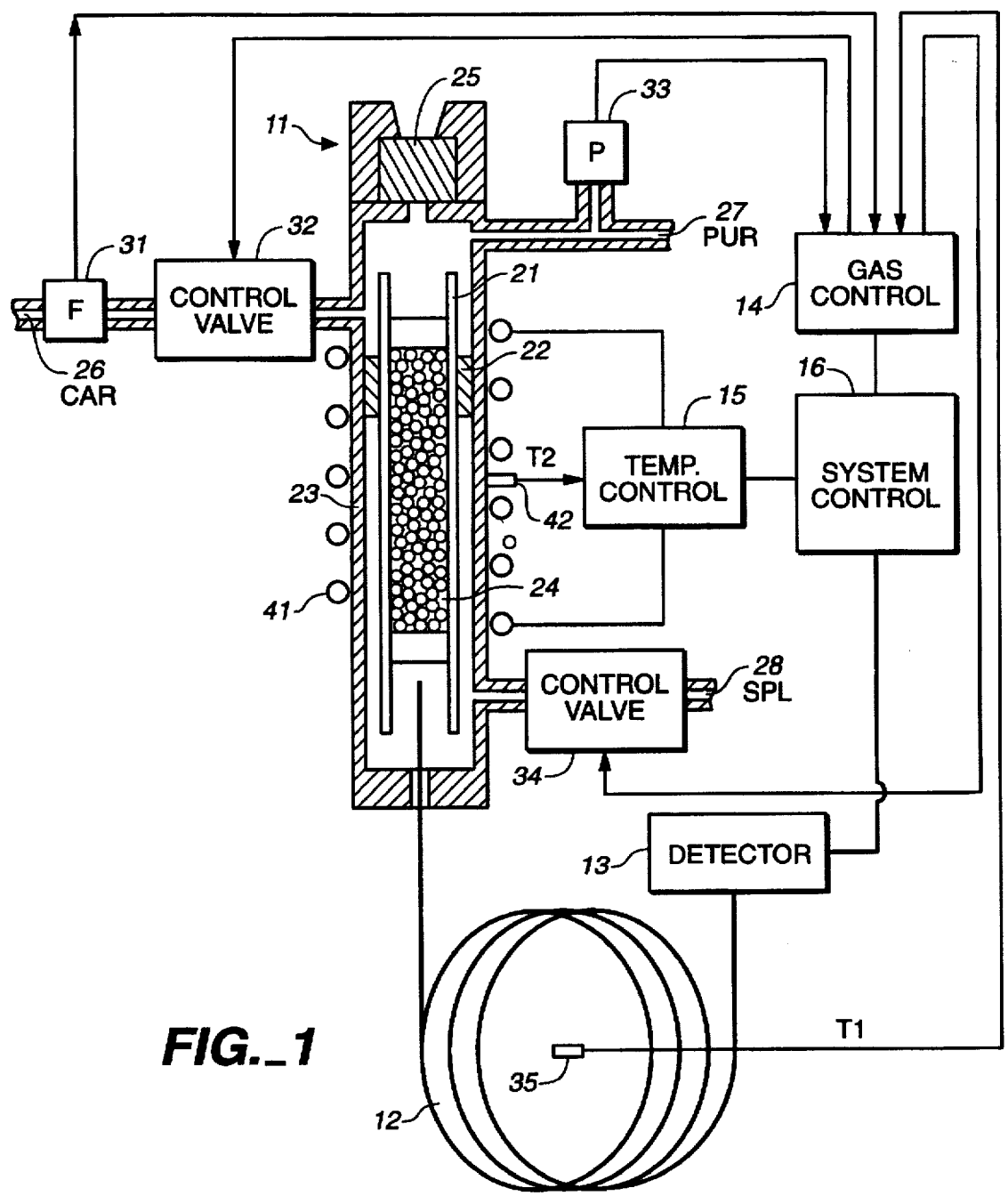
FIG._1

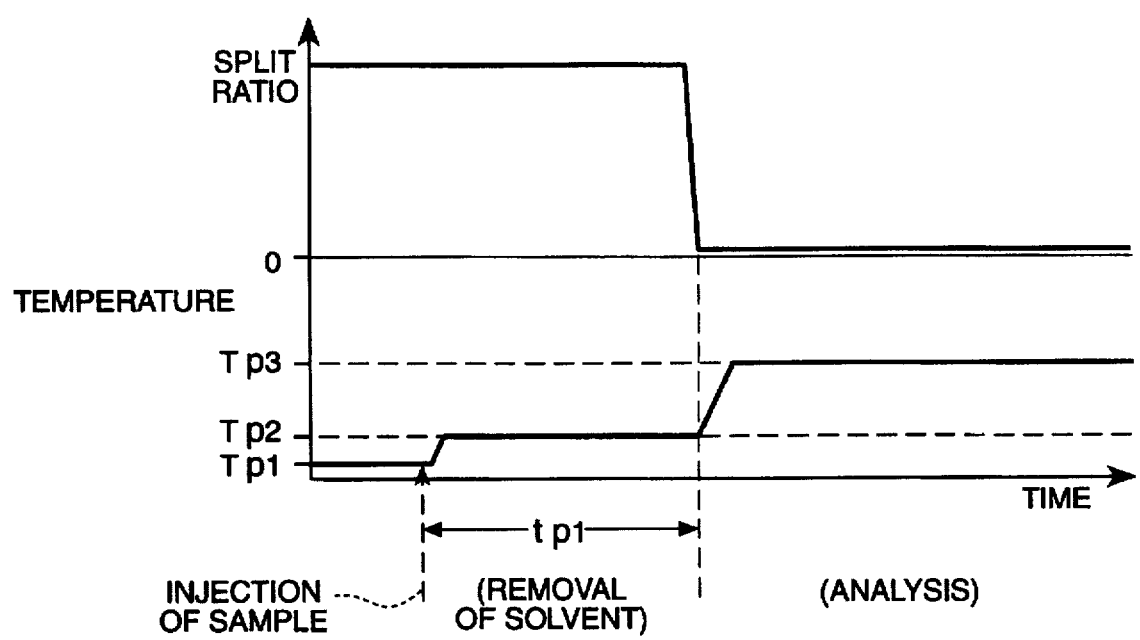
FIG._2

5,672,810

GAS CHROMATOGRAPH APPARATUS FOR A LIQUID SAMPLE CONTAINING A SOLVENT

BACKGROUND OF THE INVENTION

This invention relates to a gas chromatograph apparatus provided with a sample injection port for vaporizing a liquid sample.

It takes a long time to pass a large quantity of gas through a capillary column of the type used in gas chromatography because such a column is usually tens of meters in length while its inner diameter is less than 1 mm and usually only several hundred μm. This large resistance against a gas flow presents a serious problem when a liquid sample is vaporized for analysis by gas chromatography because there is a large amount of gas to be transported. In many situations, therefore, a so-called split analysis is carried out whereby only a portion of the carrier gas containing the sample is sent to the capillary column while the large remaining portion is discharged without ever being sent into the column.

If a split analysis is carried out with a dilute sample, or if the density of the target component (or compound) to be analyzed in the sample is very low, however, the amount of the target component to be analyzed is even smaller, and this affects the detection sensitivity adversely. For this reason, a so-called splitless method is usually used for analyzing a dilute sample.

By the splitless method, however, only about 2–3 microliters of a sample can be injected. If the injected amount exceeds this limit, a large amount of solvent will end up being introduced into the column. In view of this problem, many methods have been considered for eliminating the solvent from the sample before the vaporized sample is introduced into the column. According to the so-called moving needle injection method, for example, the liquid sample is attached to a needle and the solvent with a low boiling point is caused to evaporate and removed by a carrier gas. The needle is thereafter moved to a part of the sample injection port where temperature is maintained at a specified level, and a sample with condensed target component is desorbed from the needle and sent to the column for analysis. According to the moving pre-column injection method, the liquid sample is held by a packing material with which a tube, referred to as the pre-column, is filled. After the solvent with a low boiling point is similarly desorbed, it is moved to a part kept at a specified temperature for thermal desorption of the target component.

With these prior techniques, the structure of the sample injection port becomes complicated because the needle or the pre-column must be moved around inside, and an injection system dedicated to the sample injection becomes necessary. In such a situation, automatic sample injection systems of an ordinary kind cannot be used, and automatic analyses of many samples are difficult to carry out. Since the temperature for the desorption of a target component depends on the temperature of the sample injection port into which it is transported, the desorption process can be carried out only at one temperature.

SUMMARY OF THE INVENTION

It is therefore an object of this invention to overcome the problems of the prior gas chromatograph techniques described above.

A gas chromatograph embodying this invention, with which the above and other objects can be accomplished, is for analyzing a selected target component in a liquid sample, and may be characterized as comprising a sample injection port, a temperature control unit, a split ratio control unit, and a vaporization control unit. The sample injection port contains a pre-column filled with a packing material capable of holding a liquid sample injected into the pre-column. The sample injection port has a carrier gas inlet, a split discharge outlet, and an opening connected to a column. The temperature control unit is for controlling temperature of the sample injection port, and the split ratio control unit is for controlling the split ratio, defined as the ratio between gas flow rate to the column and the rate of the gas being discharged through the split vent. The vaporization control unit serves to control both the temperature control unit and the split control unit in coordination with each other according to the boiling points of the target component and the solvent in the liquid sample.

To start, a sample containing a target component to be analyzed, as well as a solvent, is injected into the pre-column so as to be held by the packing material therein. The temperature control unit is then controlled such that the temperature of the sample injection port is raised to a level which is above the boiling point of the solvent but below that of the target component. At the same time, the split ratio control unit is controlled such that the split ratio is increased such that as much gas as possible can be discharged through the split vent. In this manner, the solvent within the sample can be quickly removed from the sample injection port. Thereafter, the temperature control unit is controlled so as to further raise the temperature of the sample injection port above the boiling point of the target component, and the split ratio is simultaneously reduced to zero or to a very small value. In this manner, a large amount of the target component can be transported into the column, enabling an analysis with high accuracy. After the removal of the solvent from the sample injection port, the temperature inside the sample injection port and the split ratio may be varied under a program control.

In prior art gas chromatography and gas chromatography-mass spectroscopy, the amount of the liquid sample which could be injected was normally limited to only a few microliters. If an apparatus according to this invention is utilized, by contrast, over several hundred microliters of liquid sample can be injected, enabling an analysis with much higher accuracy. Since an ordinary sample injection port with an ordinary sample inlet can be used, unlike when use is made of the moving needle or moving pre-column injection method, many samples can be injected automatically according to this invention. Since desorption of the target component can be carried out at any selected temperature, once the solvent has been removed, furthermore, the present invention can be used for a large variety of analyses.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a block diagram which schematically shows the structure of a gas chromatograph embodying this invention; and FIG. 2 is a timing chart for the split ratio and the temperature inside the sample injection port at the time of sample injection when the gas chromatograph of FIG. 1 is used.

DETAILED DESCRIPTION OF THE INVENTION

FIG. 1 shows the structure of a gas chromatograph of the PTV (Programmed Temperature Vaporizer) type embodying this invention, comprising a sample injection port 11, a column 12, a detector 13, a gas control unit 14 (or "the split ratio control means"), a temperature control unit 15 (or "the temperature control means") and a system control unit 16 (or "the vapor control means"). Disposed inside the sample injection port 11 is a so-called pre-column 21, which is a glass or quartz tube with both its upper and lower ends open. The pre-column 21 is held inside the main body part 23 of the sample injection port 11 by means of a heat-resistant shield ring 22 and its interior is filled with a packing material 24 for providing a packed column. A septum 25 for sample injection is disposed at an upper part of the sample injection port 11, and one end ("the column-connecting opening") of the column 12 is inserted into the bottom part. A carrier gas flow line (CAR) 26 and a purge flow line (PUR) 27 are connected to the main body 23 above the shield ring 22, and a split flow line (SPL) 28 is connected below the shield ring 22. The opening to the carrier gas flow line 26 is herein referred to as "the carrier gas inlet" and the opening to the split flow line 28 is herein referred to as "the split vent".

The carrier gas line 26 includes a flow rate sensor (F) 31 and a flow rate control valve 32, the purge flow line 27 includes a pressure sensor (P) 33, and the split flow line 28 contains a flow rate control valve 34. They are all connected to the gas control unit 14. A temperature sensor 35 for detecting the temperature of the column 12 is also connected to the gas control unit 14. On the basis of the detected temperature T1 of the column 12, the detected inlet pressure P at the column 12 (as measured by the pressure sensor 33), and the detected flow rate R of the carrier gas, the gas control unit 14 controls the flow rate control valves 32 and 34 respectively in the carrier gas flow line 26 and the split flow line 28 such that a desired split ratio is obtained.

A heater 41 is wound around the main body 23 of the sample injection port 11, heat-generating electric current being supplied from the temperature control unit 15. A temperature sensor 42 is provided near the main body 23, and the temperature control unit 15 serves to control the supply of heat-generating current to the heater 41 according to the detection signal T2 outputted from the temperature sensor 42 such that the temperature of the sample injection port 11 will remain at a specified level.

The gas control unit 14 and the temperature control unit 15 are connected to the system control unit 16. The system control unit 16 serves to output control signals to the gas control and temperature control units 14, 15 to carry out vaporization of the liquid sample as will be described below in detail. Detection signals from the detector 13 are also transmitted to the system control unit 16 and analyzed thereby. For the convenience of the disclosure, however, description of this operation will not be presented herein.

As shown in the timing chart of FIG. 2, the inside of the sample injection port 11 is kept at a temperature $T_{p1}$ somewhat below the boiling point of the solvent before the sample is injected thereinto. A needle is then inserted and the sample is injected from the septum 25 and is caused to be held by the packing material 24 inside the pre-column 21. The gas control unit 14 is controlled to set the split ratio equal to a large ratio number such as 200–300:1 and the temperature control unit 15 is operated to increase the temperature inside the sample injection port 11 to a level $T_{p2}$ which is higher than the boiling point of the solvent but lower than that of the target component. This condition is maintained for a sufficient length of time $t_{p1}$ such that a sufficiently large portion of the solvent in the sample is quickly vented through the split flow line 28. This time period $t_{p1}$ required for the discharge of the solvent is to be determined appropriately, depending on the amount of the sample to be injected.

The split ratio is thereafter set equal to zero or to a very small ratio such as about 5:1 and the temperature inside the sample injection port 11 is raised to a higher level $T_{p3}$ above the boiling point of the target component, preferably at a rate greater than 250° C./minute. This causes all or a large portion of the target component to be thermally desorbed from the packing material 24 and transported into the column 12 to be detected by the detector 13. Although FIG. 2 shows the internal temperature of the sample injection port 11 as being kept at a constant level of $T_{p3}$ throughout the period of analysis, the temperature during this period of analysis may be varied according to a specified temperature curve by a program control.

A gas chromatograph thus structured may be characterized as controlling both the temperature inside the sample injection port 11 and the split ratio simultaneously such that only the solvent in the sample is quickly discharged first and the target component is thereafter analyzed at a lower split ratio or at a zero split ratio (that is, the splitless analysis). As a result, the injected amount of the sample can be increased significantly, making analyses with high accuracy possible. Since there is no need to move the needle or the pre-column, furthermore, use may be made of a sample injection port of an ordinary kind. In other words, this invention allows an automatic sample injection device of an ordinary kind to be used without any additional equipment.

What is claimed is:

1. A gas chromatograph for analyzing a target component in a liquid sample also containing a solvent; said apparatus comprising:

a sample injection port containing a pre-column filled with a packing material capable of holding said liquid sample injected into said pre-column, and having a carrier gas inlet, a split discharge outlet and a column-connecting opening connected to a column;

temperature control means for controlling temperature of said sample injection port;

split ratio control means for controlling the split ratio defined as the ratio between gas flow rates through said column-connecting opening into said column and through said split discharge outlet out of said sample injection port; and vaporization control means for controlling said temperature control means and said split control means in coordination with each other according to the boiling point of said target component and the boiling point of said solvent;

wherein said vaporization control means causes said temperature control means to keep the temperature of said sample injection port below the boiling point of said solvent before said sample is injected into said pre-column, causes said split ratio control means to keep the split ratio at a large value and said temperature control means to raise the temperature of said sample vaporization above the boiling point of said solvent after said sample is injected into said pre-column so as to cause a large portion of said solvent to be discharged from said sample injection port mostly through said split vent, and causes said split ratio control means to reduce the split ratio to a smaller value than said large value and said temperature control means to raise the temperature of said sample injection port above the boiling point of said target component after a specified length of time depending on the amount of said sample which was injected.

2. The gas chromatograph of claim 1 further comprising a septum which contains said liquid sample from which said liquid sample is adapted to be injected into said pre-column.

3. The gas chromatograph of claim 1 further comprising a heater and a temperature sensor for detecting the temperature of said sample injection port, said temperature control means controlling said heater according to output from said temperature sensor indicative of the temperature of said sample injection port.

4. The gas chromatograph of claim 1 wherein said split ratio control means include a control valve in a split flow line which connects to said split vent.

5. The gas chromatograph of claim 1 wherein said smaller value is zero.

6. The gas chromatograph of claim 1 wherein said temperature control means is capable of increasing the temperature of said sample injection port faster than 250° C./minute.

* * * * *